United States Patent [19]

Naudi

[11] Patent Number: 4,680,716
[45] Date of Patent: Jul. 14, 1987

[54] AUTOMATIC METHOD AND APPARATUS FOR DOSING SAMPLES

[75] Inventor: Alain Naudi, Chelles, France

[73] Assignee: U.S. Philips Corporation, New York, N.Y.

[21] Appl. No.: 676,448

[22] Filed: Nov. 29, 1984

[30] Foreign Application Priority Data

Dec. 2, 1983 [FR] France .................. 83 19290

[51] Int. Cl.⁴ .................. G06F 15/46; G01N 1/28
[52] U.S. Cl. .................. 364/468; 364/472; 378/44; 432/262
[58] Field of Search .................. 364/468, 472–473, 364/496, 500, 502, 567; 378/44–46; 423/179, 179.5; 501/33–34, 39; 432/262–265

[56] References Cited

U.S. PATENT DOCUMENTS

| | | | |
|---|---|---|---|
| 3,961,905 | 6/1976 | Rice | 432/262 X |
| 3,972,721 | 8/1976 | Hammel et al. | 501/33 X |
| 4,032,390 | 6/1977 | Rice | 432/262 X |
| 4,063,916 | 12/1977 | De Vos et al. | 501/33 X |
| 4,478,676 | 10/1984 | Belt et al. | 432/264 X |
| 4,495,155 | 1/1985 | Ricard et al. | 432/263 X |
| 4,519,092 | 5/1985 | Albert | 378/45 |
| 4,577,338 | 3/1986 | Takahashi et al. | 378/44 X |

Primary Examiner—Gary V. Harkcom
Attorney, Agent, or Firm—Paul R. Miller

[57] ABSTRACT

In an automatic sample-dosing method and machine a "bead" is formed which is to be analysed by X-ray fluorescence with, the mixture being dosed in three stages: feeding with flux material (lithium tetraborate), feeding with sample material, and feeding with flux material in such a way that the sample material does not stick to the wall of the weighing pan by making use of the relevant angles of repose.

13 Claims, 5 Drawing Figures

AUTOMATIC METHOD AND APPARATUS FOR DOSING SAMPLES

The invention relates to an automatic dosing method for dosing a mixture of a sample to be analysed and a flux, for example lithium tetraborate, in a weighing pan of a continuous-measurement balance with the dose mixture thus obtained being intended to be melted in a crucible so as to form, after cooling, a solid solution in lithium glass or "bead", which is subsequently analysed, for example by means of an X-ray fluorescence spectrometer, and the invention also relates to a machine for automatically dosing and analysing the mixture.

BACKGROUND OF THE INVENTION

The solid solution or bead technique is well-known in the cement industry and in the iron and steel industry.

Crucibles employed for fusion are known for example from European Patent Application no. 0,042,327 filed by IRSID, in which a platinum crucible and a vitreous carbon crucible are described; the induction furnace for the automatic preparation of beads from a mixture of the sample and flux is also known, for example from French Patent Application published under no. 2,381,303 and its Certificate of Addition no. 2,428,834, also in the name of IRSID.

"Bead-preparation" machines and "spectrometers" are also well-known and are commercially available, for example from the Applicant under the designations "PERL'X-2" and "PW 1600/10".

Until recently the sample-and-flux mixture was dosed manually by means of a known electronic sample-mixture balance and the transfer of the mixture into a crucible and the transfer of the bead into the spectrometer were also effected manually; however, the current trend is to automate the various operations to a maximum extent, in particular in the cement industry, as revealed in French Patent Application no. 2,485,733.

This last-mentioned Application describes an automatic sample-preparation device; and this device comprises a weighing machine which consecutively receives the sample and the flux material, and a manipulator arm for consecutively transferring the crucibles from the weighing machine to the induction furnace.

This gives rise to problems because the sample is "stickier" than the flux so that it tends to stick to the receptacle walls and also because the crucibles are very expensive so that the crucible "chain" is an expensive solution.

SUMMARY OF THE INVENTION

The invention aims at mitigating these problems.

To this end an automatic sampling method in accordance with the invention is characterized in that automatic feeding of the weighing pan is effected in the following stages:

(a) feeding with flux to a target weight FC1,
(b) feeding with sample material to a predetermined target weight EC,
(c) feeding with flux to a targer weight FC2,
   the ratio (FC1+FC2)/EC being equal to a predetermined target value RFEC,
   the targer weight FC1 being equal to four fifths of the total target weight of the flux, i.e.
   $FC1 = 4/5 \times RFEC \times EC$ with the three stages being selected so as to make an optimum use of the angles of repose of the flux and the sample material respectively in such a way that the sample material is not in contact with the weighing pan.

This enables the weighing operation to be carried out with one weighing pan whose price is substantially lower than the price of a crucible.

The method disclosed above has the advantage that the contents of the weighing pan can be poured, for example, directly into the crucible of the induction furnace with the crucible being suitably made of vitreous carbon; in this way the automatic machine embodying the inventive method comprises only one weighing pan and one crucible, which represents a substantial saving when the machine is used on an industrial scale.

BRIEF DESCRIPTION OF THE DRAWINGS

A preferred embodiment of the invention will now be described in more detail, by way of non-limitative example, with reference to the accompanying drawings.

DESCRIPTION OF THE PREFERRED EMBODIMENTS

Figure 1:
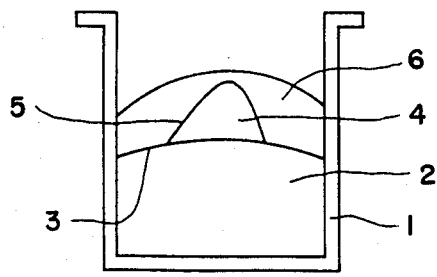
FIG. 1 shows a weighing pan.

FIG. 1 shows a weighing pan which has been filled in three stages in accordance with the invention so as to make an optimum use of the respective angles of repose.

In the first stage (a) the pan 1 receives a layer of flux 2 whose surface 3 is slightly inclined in conformity with the angle of repose of lithium tetraborate, which is a rather "fluid" material; in the second stage (b) the pan 1 is loaded with a layer of the sample material to be analyzed 4 whose surface 5 is slightly more pointed, in such a way that its base is not in contact with the side walls of the weighing pan 1; in the third stage (c) the pan 1 is loaded with a layer of flux 6 which settles between the sample layer 4 and the walls of the weighing pan and which is the complement of the weight of the flux layer 2 so as to bring the mixture thus obtained in conformity with the desired values.

The weighing pan is fed from three hoppers equipped with vibrators and chutes; the pan is placed on the platform of an electronic programmable continuous balance whose readings control the action of the vibrators; the various feeding devices are not shown because they are well-known to those skilled in the art of automation, the balance being for example available from METLET and the associated vibrators from Ste BERNAY; as an example, a balance may be chosen which continuously measures the weight with an accuracy of 0.01 g and, when the vibrators have been switched off, i.e. when the contents of the pan stabilised, provides a measurement accuracy of 0.001 g.

After having programmed the system in conformity with the instructions given by the manufacturer of the programmable balance, this yields (a) for the flux layer 2 a real weight FR1 which is very close to a target weight FC1; when the flux vibrator is switched off a measurement with an accuracy of 0.001 g is obtained for FR1, the measured value being stored in a memory;

(b) for the sample layer 4 a real weight BR very close to a target weight EC; when the sample vibrator is switched off a measurement with an accuracy of 0.001 g is obtained for ER, which value ER is stored and is also used for calculating a desired total weight, or target weight, of flux, to calculate the complementary flux target weight FC2, taking into account the value of FR1;

(c) for the flux layer 1 the flux vibrator is again switched on to obtain a real flux weight FR2 which is as close as possible to the target weight FC2 which has been computed as described above.

Preferably, the ratio $FC1=4/5\times(FC1+FC2)$ is adopted to make an optimum use of the angles of repose.

The final contents of the pan is checked for conformity with the required predetermined weight and proportion (dosage) of the mixture; if the final contents are correct, dosing is terminated; if it is not, dosing is discontinued, the weighing pan is emptied, and a new dosing operation is started. It is to be noted that a dosing operation will be incorrect only due to a surplus of one of the components, for example if the granule size is too large, because the corresponding vibrator provides immediate compensation for a deficiency in weight.

The ratio $(FR1+FR2)/ER=RFEP$ should be as close as possible to a target value RFEC chosen from values between, for example, 3 and 15; the required accuracy should be between ±0.1 % and ±2 %; the choice of these parameters depends on the nature of the sample and the type of industry: cement industry, iron and steel industry, etc.

In order to improve the dosing accuracy it is advantageous to split stage (b) and stage (c) into two steps, namely:

for stage (b) the steps (b') fast-rate feeding with sample material to obtain a targer weight EC1 equal to a fraction, for example a third, of the target weight EC, and (b) slow-rate feeding with sample material to obtain a target weight EC2 equal to the complement of the fraction EC1, i.e. for example two thirds, of the target weight EC, for the stage (c) the steps (c') fast-rate feeding with flux to obtain a target weight FC 21 equal to a fraction, for example three quarter, of the target weight FC2, the feeding rate of stage (a) then being equal to the fast rate of stage (c'), and (c) slow-rate feeding with flux to obtain a target weight FC22 equal to the complement of the fraction FC21, for example a quarter, of the target weight FC2. In this way feeding is effected without loss of time and with precision. The change in vibrator rate is obtained under control of the continuous measurement balance; two-rate vibrators are available from the above-mentioned or other manufacturers.

These operations are controlled by means of a programmable automatic control device which is not described and not shown because it is well-known to those skilled in the art of automation.

This automatic control device can be connected normally to the continuous electronic balance and to the vibrators.

In the machine embodying the methods only one crucible is required, which is a substantial saving. For pouring the contents of the weighing pan into the crucible use is made of a manipulator arm equipped with a gripper 10 with assembly being moved by actuators controlled by the programmable automatic control device. The various elements which are required can be found in, for example, the catalogue of the NEW-MAT company for the gripper and the CPOAC company for the actuators and the solenoids; thus, as shown schematically in FIG. 2, the weighing-pan manipulator arm 11 transfers the weighing pan 1 from its weighing position (1) to a discharge position (2) above the crucible 12 under control of the automatic control device, not shown. Since the crucible 12 is practically always hot (approximately 700° C.) during industrial use it is advantageous, in accordance with the invention, to arrange an internally polished (for example by 4 μm diamond) stainless-steel funnel 13, between the weighing pan and the crucible to guide the mixture into the crucible. This prevents the mixture from being "blown away" by turbulent hot air in the crucible. The funnel 13 is mounted on the manipulator arm 11 so as to be rotatable about a vertical axis and translatable in a vertical direction. The vertical translation which is controlled by a solenoid, which in its turn controlled by the automatic control device, enable the funnel to be lowered into and be raised from the crucible and to shake the funnel in order to ensure that the entire mixture is discharged into the crucible, which is also promoted by the internal polishing of the funnel. The rotation about a vertical axis ensures that the funnel cannot damage the balance 14 when the arm is in position 1, ensuring that the funnel being subsequently returned to the correct position for pouring the mixture into the crucible by a simple return spring, as shown in FIG. 3.

Figure 4:
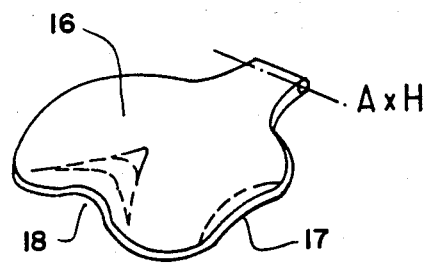
FIG. 4 shows the lid of the crucible.
Figure 2:
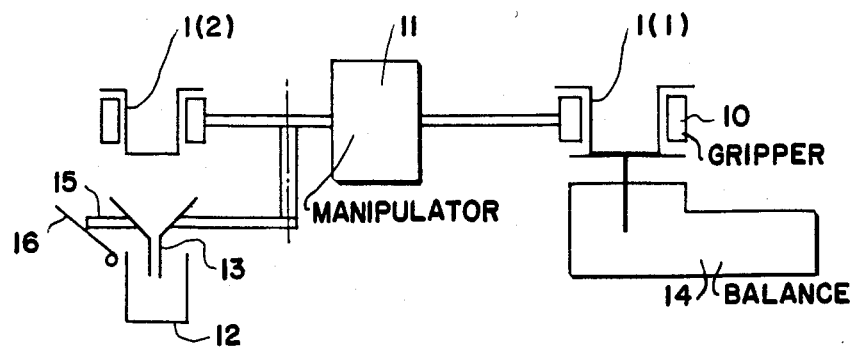
FIG. 2 shows schematically the weighing-pan manipulator.
Figure 3:
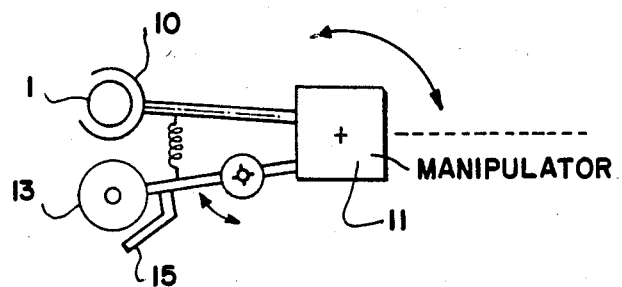
FIG. 3 is a plan view of a part of the manipulator.

Suitably, the crucible is equipped with a lid 16, FIG. 2, which must be opened to fill the crucible with the mixture and which must be closed for the rest of the time. The lid is opened under control of a pin 15, FIGS. 2 and 3, which actuates the lid 16 by cooperation with a projection 17 on this lid, FIG. 4. The lid then pivots about its horizontal axis (AXH); during the fusing operation the lid is closed automatically as a result of the oscillating movements of the crucible, as described in that above-mentioned Patent Applications.

Suitably, the crucible has a chimney-like portion 18 to facilitate the escape of gases; in view of the requirements imposed on the lid it is advantageous to use an alloy of platinum and, for example 10%, of rhodium in order to ensure that the lid has a higher resistance to deformation than it would have if it were made of pure platinum.

Figure 5:
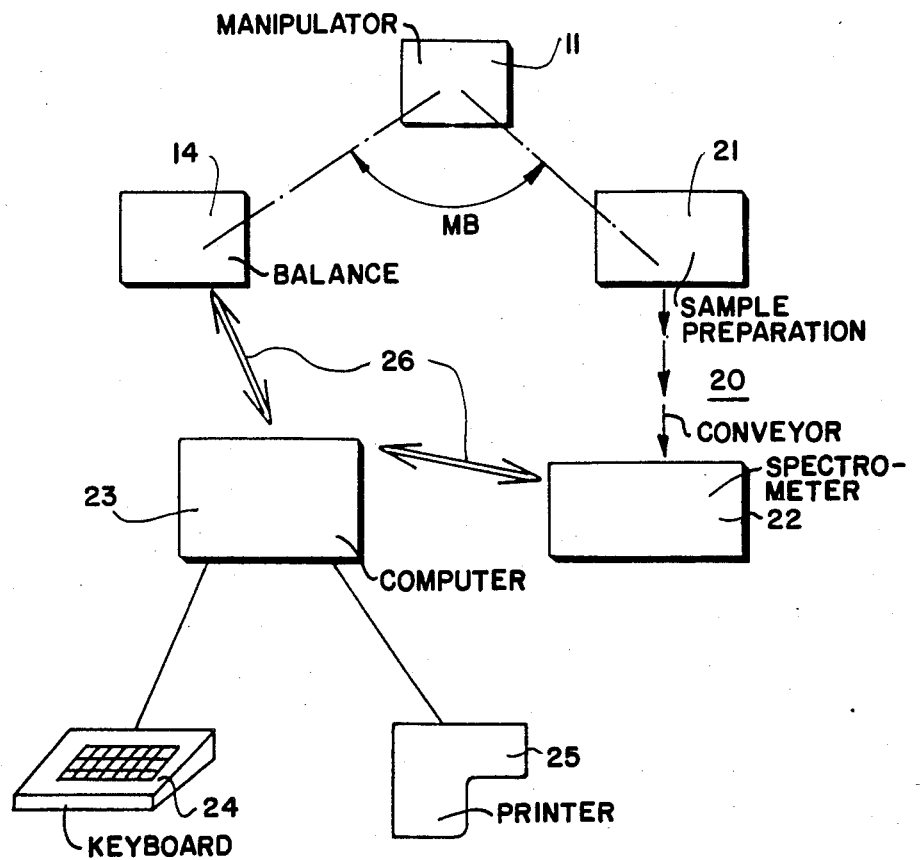
FIG. 5 shows schematically the entire machine.

In order to take full advantage of the automatic operation, it is advantageous to use a transfer device, comprising known means of the conveyor-belt type 20, FIG. 5, for transferring the bead obtained after fusing and cooling from the "bead-preparation" machine 21 to the spectrometer 22, for example type "PW 1600/10" commercially available from the Applicant. The, the arrangement comprising the balance 14, the bead-preparation machine 21 and the spectrometer 22 with the associated transfer devices such as the manipulator arm 11 and the conveyor belt 20 is a fully automatic arrangement which is synchronized and controlled by a computer 23 provided with transmission means 26 for receiving, processing and storing the results of the various operations, in particular the weights, or dosage, and the analyses. The predetermined parameters for these operations may be generated by means of a keyboard 24 and the results may be visualized by means of a printer 25 or a display screen; the results may also by utilized for automatically controlling the manufacture of the product being analysed.

In the automatic machine thus obtained (FIG. 5) the entire sequence of operations takes about eleven minutes. This time depends in particular on the choice made from the five possible weighing programs, the six possible computing programs programmes, and the sixty measuring programs of the spectrometer. The analysis performed by the spectrometer takes a comparatively short time and therefore it is advantageous that the computer does not block the spectrometer during the weighing and fusing operations in order to enable the spectrometer to be used for further operations thereby ensuring an optimum use of this apparatus.

What is claimed is:

1. An apparatus for automatically dosing a mixture of a sample and a fluxing comprising
    first means for continuously weighing sample material and a flux, first hopper means having a vibrator and chute for feeding said flux, second hopper means having a vibrator and chute for feeding said sample material, second means for automatically controlling said weighing of said sample material and said flux, a weighing structure controlled by said second means, third means having a manipulator arm with a gripper for manipulating said weighing structure, said vibrator for said first hopper means being a two-rate vibrator and said vibrator for said second hopper means being a two-rate vibrator, and said second means being programmable to select one of sample weight EC, a tolerance between a real sample weight relative to EC, a predetermined value RFEC of a ratio of flux weight FC1+FC2 to said sample weight EC, and a maximum permissible deviation between RFEC and an obtained value of said ratio.

2. An apparatus according to claim 1, wherein said sample weight EC is in a range between 0.3 gram and 1.5 gram.

3. An apparatus according to claim 1, wherein said tolerance between said real sample weight relative to EC is in a range between ±0.001 gram and ±0.01 gram.

4. An apparatus according to claim 1, wherein said value RFEC ranges between 3 and 15.

5. An apparatus according to claim 1, wherein said maximum permissible deviation ranges between ±0.1% and ±2%.

6. An apparatus according to claim 1, wherein an induction furnace, a crucible and crucible lid are provided, said crucible and crucible lid being rotatable about a horizontal axis, wherein said manipulator arm transfers said weighing structure from a weighing position to a second position above said crucible, said second means tilting and shaking said weighing structure to discharge a dosed mixture of said sample material and said flux, said second means returning said weighing structure to said weighing position, and wherein said crucible is of vitreous carbon and said crucible lid is an alloy of platinum and 10% rhodium, said crucible lid having a chimney for discharging gases and a projection, said manipulator arm including a pin-type structure cooperating with said projection to open said crucible lid.

7. An apparatus according to claim 6, wherein said third means includes a movable supporting device for an internally polished stainless-steel funnel, said funnel being disposed between said weighing structure and said crucible to guide said sample material and flux mixture toward a bottom of said crucible, and said funnel being horizontally tilted during weighing, said funnel being vertically lowered into said crucible, and said funnel being vertically shaken after tilting said weighing structure to ensure complete transfer to said crucible, said second means controlling said third means.

8. An apparatus according to claim 7, further comprising an X-ray fluorescence spectrometer and transfer means for transferring each mixture from said crucible after cooling to said spectrometer,
    wherein computer means are provided for synchronizing and controlling said second means, said third means to transfer said mixture to said crucible, said induction furnace, and said transfer means, said computer means receiving information for processing, storing, editing and displaying information of weighing and analyzing.

9. An apparatus according to claim 8, wherein an entire sequence of operations are performed in substantially eleven minutes, said computer means enabling said spectrometer to be used for a small portion of said eleven minutes, and to be used for other purposes during weighing and fusing.

10. A method for automatically dosing a mixture of a sample and a flux comprising
    automatically feeding flux to a weighing pan, said flux being fed to a first weight of FC1,
    automatically feeding sample material to said weighing pan, said sample material being fed to a weight of EC,
    again automatically feeding said flux to said weighing pan, said flux being fed to a second weight of FC2,
    wherein a ratio of FC1+FC2/EC is equal to a predetermined value, and wherein said first weight FC1 is equal to four fifths of a total weight of said flux,
    said steps of automatically feeding said flux and sample material being carried out to prevent contact with said weighing pan by said sample material.

11. A method according to claim 10, wherein said steps of feeding is automatically discontinued upon measuring a surplus weight of said sample material or said flux.

12. A method according to claim 10 or 11, wherein said step of automatically feeding said sample material is carried out by fast-rate feeding said sample material to a first weight of EC1, said first weight being a fraction of EC, and slow-rate feeding said sample material to a second weight EC2, said second weight being a complementary fraction weight of said first weight, and wherein said step of again automatically feeding said flux is carried out by fast-rate feeding said flux to a weight of FC21 being a fraction of said second weight of FC2, said automatic feeding of said flux to said first weight of FC1 being at a rate equal to said fast-rate feeding of said flux to a fraction of FC2, and slow-rate feeding said flux to another weight FC22, said another weight FC22 being equal to the complement of FC21.

13. A method according to claim 12, wherein said steps of slow-rate feeding are discontinued upon exceeding said weights EC2 and FC22.

* * * * *